US011857199B2

(12) United States Patent
Mac An Tuile et al.

(10) Patent No.: US 11,857,199 B2
(45) Date of Patent: Jan. 2, 2024

(54) SURGICAL SAW SYSTEM INCLUDING A RECIPROCATING SAW BLADE CARTRIDGE

(71) Applicant: Stryker European Operations Holdings LLC, Kalamazoo, MI (US)

(72) Inventors: Conor Mac An Tuile, Muine Bheag (IE); David Tallon, Shanagarry (IE); David Goldenberg, Mattawan, MI (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 173 days.

(21) Appl. No.: 17/478,327

(22) Filed: Sep. 17, 2021

(65) Prior Publication Data
US 2022/0015771 A1 Jan. 20, 2022

Related U.S. Application Data

(63) Continuation of application No. 16/062,727, filed as application No. PCT/US2016/066981 on Dec. 15, 2016, now Pat. No. 11,141,168.
(Continued)

(51) Int. Cl.
*A61B 17/14* (2006.01)
*A61B 17/15* (2006.01)

(52) U.S. Cl.
CPC .......... *A61B 17/144* (2016.11); *A61B 17/142* (2016.11); *A61B 17/15* (2013.01)

(58) Field of Classification Search
CPC ...... A61B 17/144; A61B 17/15; A61B 17/142
See application file for complete search history.

(56) References Cited

U.S. PATENT DOCUMENTS

| 1,838,125 A | 12/1931 | Wirtz |
| 4,020,555 A | 5/1977 | Hedrick |

(Continued)

FOREIGN PATENT DOCUMENTS

| DE | 102008063239 A1 | 6/2010 |
| EP | 1106318 A2 | 6/2001 |

(Continued)

OTHER PUBLICATIONS

English language abstract and machine-assisted translation for DE102008063239 extracted from espacenet.com on Jun. 13, 2018; 34 pages.
(Continued)

*Primary Examiner* — Julian W Woo
(74) *Attorney, Agent, or Firm* — Howard & Howard Attorneys PLLC

(57) ABSTRACT

A surgical saw system including a saw, a blade cartridge and an attachment. The saw including a housing and a reciprocating shaft. The blade cartridge that may be removably coupled to the saw includes a bar and a rack. The bar includes a first holding feature. The rack is moveably disposed within the bar, and is configured to removably couple to the reciprocating shaft of the saw. The attachment is disposed between and connecting the bar of the blade cartridge to the saw. The attachment may include a coupling feature in selective releasable engagement with the first holding feature of the bar to hold the bar static relative to the saw. The blade cartridge may also include a drive link that extends from reciprocating shaft of the saw and the rack for imparting the reciprocal motion of the reciprocating shaft to the rack.

20 Claims, 11 Drawing Sheets

Related U.S. Application Data

(60) Provisional application No. 62/268,536, filed on Dec. 17, 2015.

(56) References Cited

U.S. PATENT DOCUMENTS

| | | | |
|---|---|---|---|
| 6,001,115 | A | 12/1999 | Ahola et al. |
| 6,302,406 | B1 * | 10/2001 | Ventura ................ A61B 17/144 |
| | | | 606/177 |
| 8,080,011 | B2 | 12/2011 | Harp |
| 8,444,647 | B2 | 5/2013 | Walen et al. |
| 8,672,943 | B2 | 3/2014 | Fisher et al. |
| 9,101,992 | B2 | 8/2015 | Zhou et al. |
| 9,566,074 | B2 | 2/2017 | Milburn et al. |
| 11,141,168 | B2 | 10/2021 | Mac an Tuile et al. |
| 2006/0009796 | A1 | 1/2006 | Carusillo et al. |
| 2013/0204255 | A1 | 8/2013 | Milburn et al. |
| 2014/0190023 | A1 | 7/2014 | Vitantonio et al. |
| 2020/0261100 | A1 | 8/2020 | Mac An Tuile et al. |

FOREIGN PATENT DOCUMENTS

| | | |
|---|---|---|
| WO | 2006017066 A2 | 2/2006 |
| WO | 2017106533 A3 | 9/2017 |

OTHER PUBLICATIONS

International Search Report and Written Opinion for PCT/US2016/066981 dated May 2, 2017; 13 pages.

* cited by examiner

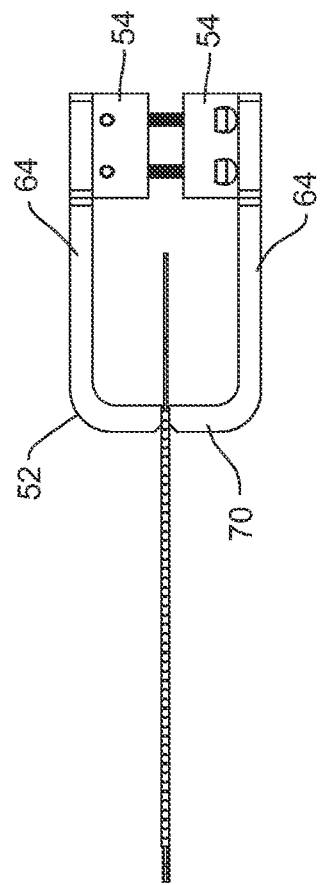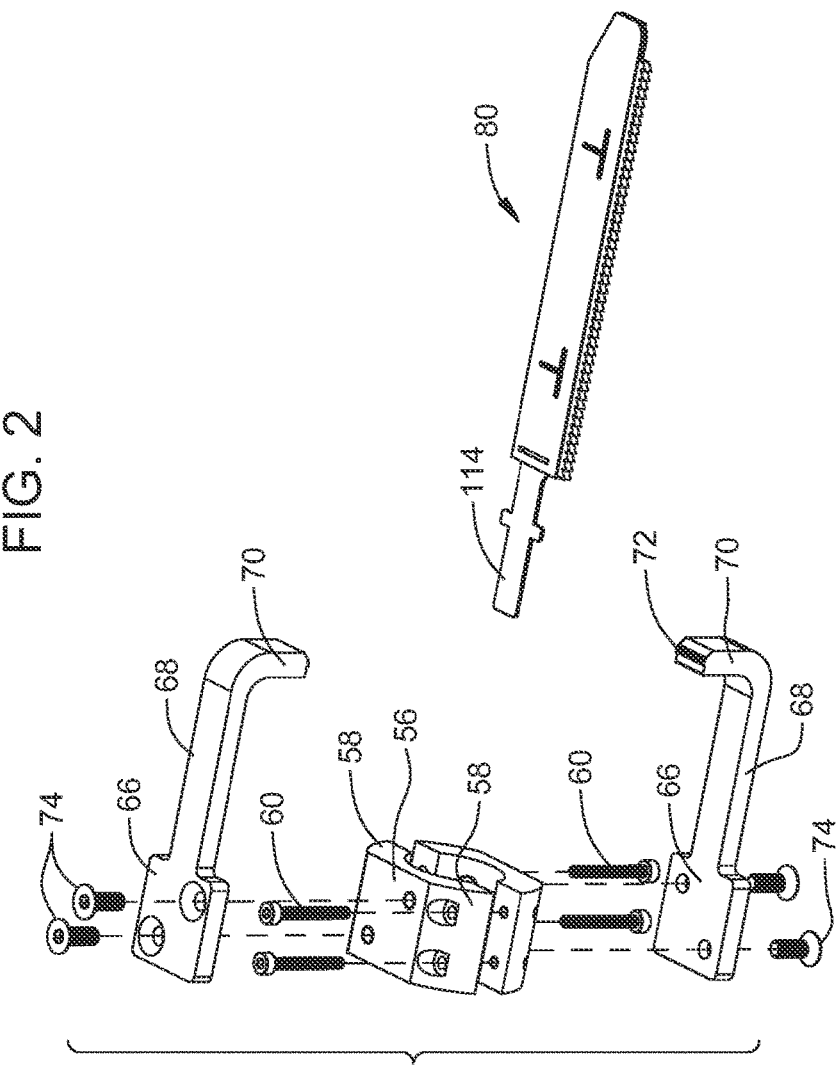

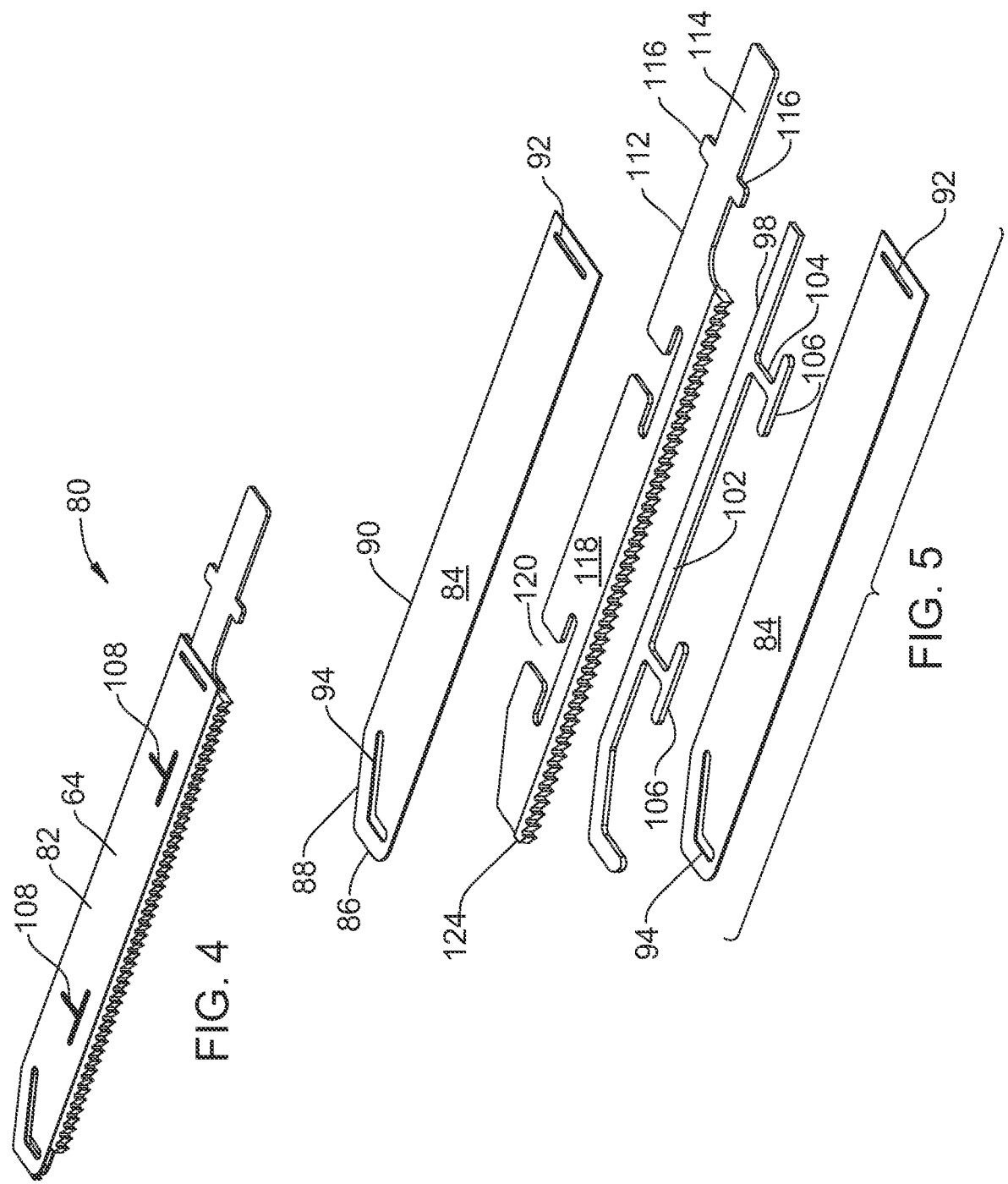

SURGICAL SAW SYSTEM INCLUDING A RECIPROCATING SAW BLADE CARTRIDGE

CROSS-REFERENCE TO RELATED APPLICATIONS

This patent application is a continuation of U.S. patent application Ser. No. 16/062,727 filed Jun. 15, 2018, which claims priority to and all advantages of International Patent Application No. PCT/US2016/066981 filed Dec. 15, 2016, which claims priority to and all advantages of U.S. Provisional Patent Application No. 62/268,536 filed Dec. 17, 2015, the entire contents of which are incorporated herein by reference.

FIELD OF THE INVENTION

This application is generally related to a reciprocating saw blade. More particularly, this application is directed a reciprocating saw blade cartridge that is releasably mounted to the saw with which the cartridge is used. The cartridge includes a static bar to which a reciprocating rack is attached.

BACKGROUND OF THE INVENTION

In a surgical procedure, it is sometimes necessary to use a saw to remove tissue, including bone and cartilage. Often a powered saw is used to perform this procedure. Attached to the saw is a saw blade. A drive assembly internal to the saw oscillates the blade in a back and forth motion. Some blades move back and forth along their longitudinal axes. This type of blade is known as a reciprocating saw blade. This type of blade is provided with teeth that extend outwardly from a side edge of the blade body. Many reciprocating saw blades are designed to remove hard tissue, bone.

Reciprocating saw blades generally work well for the purposes for which they are designed. These saw blades are able to cut the bones to which they are applied.

However, there are times when use of a reciprocating saw blade results in undesirable side effects. One such side effect is due to the fact that, when a reciprocating saw blade is positioned to cut some types of tissue, the body of the blade presses against soft tissue that is not targeted for removal. This can occur when a reciprocating saw blade is used in oral surgery to remove a portion of the jaw. The body of a reciprocating saw blade may also press tissue when the blade is used in small bone orthopedic surgery, surgery of the hand or foot and ankle.

A problem can arise in these types of surgical procedure because a reciprocating saw blade can move back and forth at a rate of between 10,000 and 15,000 cycles per minute. This rapid movement of the blade can foster appreciable friction-induced heating of the soft tissue against which the blade body is pressed. The heating of this tissue can sometimes damage the tissue. If the damages tissue is part of the nerve system, a muscle or a ligament, the effects of the damage can especially undesirable.

Also, there are procedures in which, owing to how the reciprocating saw blade is positioned in the tissue, it is extremely difficult, if not impossible, for the surgeon to see the end section of the blade. For example in a rhinoplasty procedure a reciprocating saw blade is used to remove a portion of the nose bone. In this type of procedure, to avoid the ready appearance of a scar, the blade is typically inserted into the nose through the flap of the skin between the nostrils. In some hip replacement procedures a reciprocating saw blade may likewise be positioned so it can be difficult to see the free end of the blade. Again, it should be understood that a reciprocating blade moves back and forth. In procedures in which the distal section of the blade is hidden from view, there is a possibility that this section of the blade repeatedly presses against tissue that is not targeted for removal. This back and forth movement of the tissue can stress the tissue to the point at which it tears or is otherwise damaged.

In some procedures, to ensure a planar cut, it is a common practice to insert the reciprocating saw blade in a device known as a resection guide (not illustrated). This guide is sometimes referred to as a guide block or a cutting jig. The resection guide has a slot in which the blade is inserted. The device is held static relative to the tissue to be cut. Since the device is held static, the blade is blocked from movement out of the plane of the slot. By so restricting the movement of the blade, the surface of the bone left after the cut is formed s planar in shape. This facilitates the proper seating of an implant, which typically has its own planar surface, against the bone. When a reciprocating saw blade moves back and forth in the resection guide, the body of the blade invariably rubs against the inner surfaces of the guide that define the cut. This metal-against-metal rubbing results in the rubbing away of the material forming the resection guide. One adverse effect of this wear is that at least some of the fine dust of metal generated by this wear invariably lands on the exposed internal tissue of the patient. This means that after the cut is formed and the resection guide is removed, care must be taken to clean the tissue to remove these debris so as to prevent them causing harm to the patient. A second adverse effect of this wear is that, over time, the wear can appreciably widen the slot or slots formed in the resection guide. If these slots become too wide relative to the blade, the resection guide may no longer function as a useful guide for ensuring that the cut formed by the reciprocating blade has the desired shape.

US Pat. Pub. US 2006/0009796 A1/PCT Pub. WO 2006/017066 A2, the contents of which are incorporated herein by reference, discloses a type of a saw blade known as a sagittal saw blade. A sagittal saw blade has teeth that pivot back and forth around an axis that extends through the plane of the blade. One of the sagittal saw blades disclosed in this publication has a blade head that extends laterally outwardly from the side of a static blade bar. The blade head pivots around an axis that extends through the opposed major surfaces of the blade bar. This blade head, when pivoted, cuts the tissue against which the teeth are pressed. However, the length of the cut formed by this blade is relatively short, typically less than one-third length of the cut that would be performed by a compatibly sized conventional reciprocating saw blade. It therefore can take an appreciably longer time to make a cut with this cartridge than it would in order to make the same length cut using a conventional reciprocating saw blade.

A species of the reciprocating saw blade is the sternum saw. As implied by its name, the sternum saw blade is used to cut the sternum. Typically, it is necessary, to cut, separate, the sternum so the surgeon can gain access to the tissue and organs below the sternum. These organs include the heart and lungs. When cutting the sternum, it is naturally desirable to avoid positioning the saw blade so the blade strikes, cuts, the organs and tissue immediately below the blade. To prevent this undesirable result, a sternum saw blade is mounted in a guard. A foot extends outwardly from the free end of this guard. This foot, in comparison to a narrow width blade, is relatively wide. During the process cutting the sternum, the surgeon holds the saw so the foot of the sternum guard presses against the undersurface of the sternum. The foot functions as a stop that ensures that, as the blade is advanced along the sternum, the blade cuts completely through the sternum from the outer surface to the undersurface. Further, by ensuring that the blade is so positioned, the guard ensures that the blade does not become so positioned that, as the blade is advanced the blade cuts the organs and tissues that underlying the sternum.

Sternum guards work well for the purpose for which they are designed. A problem with some sternum guards is that is that they are designed to be used with saws especially designed to hold these guards. This means a surgical facility in which the sternum is to be cut is required to have one or more of the special saws, called sternum saws, available. The facility may be required to have these saws available even though these saws have essentially no use outside of performing this one specific procedure.

SUMMARY OF THE INVENTION

This disclosure describes a new and useful reciprocating saw blade. The reciprocating saw blade is constructed to minimize the extent to which moving components of the blade other than the teeth, press against tissue. Some versions of the saw blade are further constructed to be used as a sternum blade without requiring the use of a supplemental sternum guard.

The saw blade is referred to as a cartridge. The cartridge includes an elongated bar. The bar includes features that facilitate the releasable attachment of the bar to the saw used to actuate the blade. One side of the bar is open.

The cartridge also includes a rack. The rack has a base that is moveably disposed in the bar. A portion of the rack extends to the opening in the side of the bar. The rack also includes a set of teeth. The teeth extend outwardly from the section of the bar adjacent the opening in bar. The teeth are wider in depth than the base of the rack. More particularly, have sufficient width so that when the rack is reciprocated and the teeth pressed against tissue, the teeth form a kerf of sufficient that the cartridge is able to advance through the kerf.

The rack and bar may be formed with complementary features that retain the rack in the bar while allowing the rack to move linearly in the bar.

Some versions of the cartridge may be formed to have a foot that protrudes outwardly from the opposed major surfaces of the bar. This foot functions in a manner similar to the foot of a sternum guard. Thus the foot functions as a stop to facilitate the proper positioning of the cartridge relative to the bone the cartridge is employed to cut.

This application is also directed to an attachment that can be used to couple the above-described blade cartridge to a conventional saw. A conventional saw is understood to be a saw that can be used to reciprocate a conventional reciprocating saw blade. The attachment includes a body. The body includes features for releasably holding the body static to the distal end of a conventional saw. Attached to the body is a coupling feature. The coupling feature is shaped to engage with a complementary coupling feature integral with the bar of the cartridge so as to releasably hold the bar static to the attachment. The attachment coupling feature may be a member dimensioned to seat in a void formed in the bar. The coupling feature may alternatively be an opening or other void in the body that receives the complementary coupling feature integral with the bar.

This application also discloses a saw specifically for use with the disclosed blade cartridge. This saw has a feature for engaging the bar of the cartridge to releasably hold the bar static to the body of the saw.

BRIEF DESCRIPTION OF THE DRAWINGS

The following Detailed Description is to be read with the accompanying drawings in which:

FIG. 2 is a top view of how a reciprocating blade cartridge is attached to the associated saw;

FIG. 3 is an exploded view of the grasping assembly that holds the reciprocating blade cartridge to the saw;

FIG. 4 is a perspective view of the reciprocating blade cartridge;

FIG. 5 is an exploded view of the reciprocating blade cartridge;

DETAILED DESCRIPTION

I. First Embodiment

Figure 1:
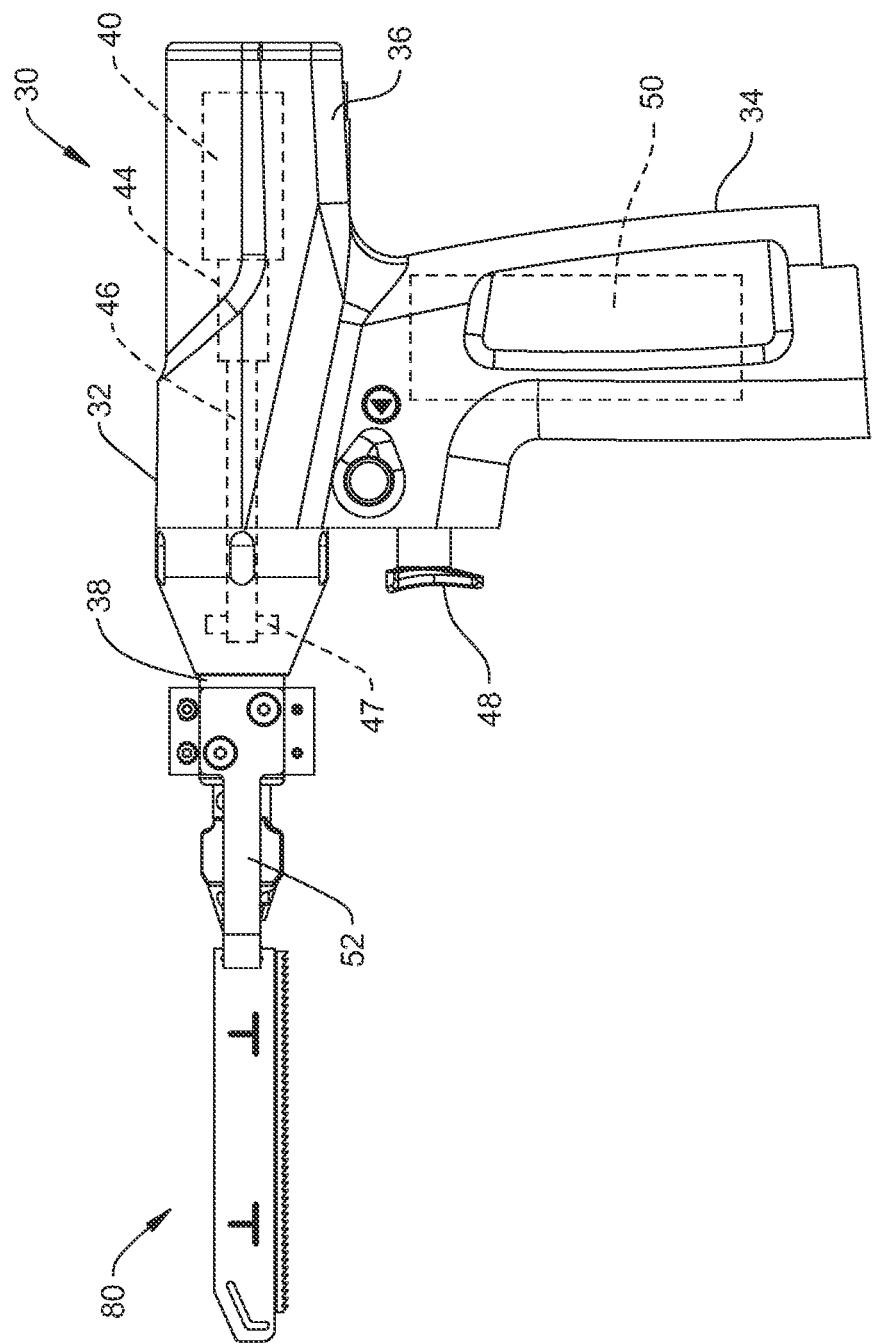
FIG. 1 is side view of a reciprocating saw to which a reciprocating blade cartridge is attached.

FIG. 1 illustrates a surgical reciprocating saw 30 to which a complementary reciprocating blade cartridge 80 is removably attached. The saw 30 has a pistol shaped body or housing 32. The saw housing 32 includes a grip 34. A barrel 36 is formed integrally with handgrip 34. The barrel 36 extends proximally, rearwardly, from and distally forward of the handgrip 34. (Here, "proximally" is understood to mean towards the surgeon holding the saw 30, away from the surgical site to which the blade cartridge 80 is applied. "Distally" is understood to mean away from the surgeon and towards the site to which the blade cartridge 80 is applied.) A nose 38 projects forward from the barrel 36 at a distal end of the housing 32.

Internal to the saw barrel 36 is a motor, represented by a dashed rectangle 40 and a reciprocating shaft, represented by dashed rectangle 46. A transmission, represented by dashed rectangle 44, is located between the motor 40 and reciprocating shaft 46. The transmission converts the rotational movement of the motor rotor into motion that reciprocates the shaft back and forth. Here "reciprocation" is understood to mean a repetitive proximal-to-distal-to-proximal motion along the longitudinal axis of the component under discussion. The distal end of the reciprocating shaft 46 is provided with engagement features that facilitate the removable coupling of the below discussed cartridge rack 112 to the shaft. The exact structure of these engagement features are not part of the invention, and may be readily provided by one skilled in the art. By way of an example, the shaft 46 may be provided with openings designed to receive holding features, e.g., complementary components, integral with the rack. A chuck, represented by dashed ring 47, may be fitted to the distal end of the shaft. The chuck 47 may hold the holding features integral with the rack 112 to the shaft.

The motor 40 internal to the saw may be a DC motor. A battery (not illustrated) may be attached to the base of the saw handgrip 34. A trigger 48 extends forward from the distally directed face of the handgrip 34. Internal to the handgrip is a control module represented by dashed rectangle 50. The control module 50 is configured to control the sourcing of the current from the battery or other power supply to the motor 40. The control module also includes a transducer that monitors the actuation of the trigger 48. Based on the actuation of the trigger 48, the control module 50 regulates the application of current to the motor 40 so as to regulate the actuation of the saw 30 and by extension, the actuation of the blade cartridge 80.

Many versions of saw 30 are configured to reciprocate a conventional reciprocating saw blade (not illustrated). The chuck 47 may be designed to hold a conventional, i.e. prior art, reciprocating saw blade (not illustrated) to reciprocating shaft 46 so the blade can be reciprocated by the shaft 46.

An attachment 52, seen best in FIG. 2 and FIG. 3, is removably secured to the saw nose 38. The attachment 52, together with the saw 30 and the blade cartridge 80, may collectively comprise a first example saw system. The attachment 52 releasably holds the below described bar 82 of the blade cartridge 80 to the saw 30. Attachment 52 includes two shells 54. Shells 54 form the body of the attachment 52. Each shell 54 includes a planar base 56 and two wings 58 that extend outwardly from opposed sides of the base 56. Each shell 54 is shaped so that as the wings 58 extends away from the shell base, the wings curve away from the base. When the saw 30 is assembled, shells 54 are placed on the opposed sides of the nose 38 so the ends of the wings 58 of each shell 54 face the ends of the wings of the other shell. Bolts 60 extends through each wing 58 to the opposed adjacent wings. Bolts 60 clamp the shells 54 together, the bolts and shells collectively defining a clamping assembly, i.e., an example first coupling feature, to hold the shells 54 around the opposed sides of the nose 38. Shells 54 and bolts 60 thus releasably hold the attachment 52 static to the nose 38.

A hand 64, also part of the attachment 52, extends distally forward from each shell 54. Each hand 64 includes a rectangular palm 66, one palm identified. Palms 66 are dimensioned to seat over the exposed surface of the shell 54 from which the hand 64 extends. Screws 74 hold each palm 66 to the associated shell 54. (Not identified with reference numbers are the openings in the shells 54 and hands 64 through which the screws 74 extend. A finger 68, also part of each hand 64, extends forward from each palm 66. Each finger 68 has a main section (not identified) that extends along a longitudinal axis that is parallel to the proximal-to-distal longitudinal axis through the saw barrel 36. Each finger 68 has a tip 70 that extends perpendicularly to the longitudinal axis of the main section of the finger. A small rib 72, an example second coupling feature, protrudes forward from end face of each finger tip 70. The clamping assembly 58 and 60 is arranged so that when the clamping assembly is fitted to the saw, the opposed ribs 72 face each other.

From FIGS. 4 and 5 it can be seen that the reciprocating blade cartridge 80 includes a static bar 82 in which a rack 112 is moveably mounted. Bar 82 includes two plates 84. The plates 84 are generally rectangular in shape. Each plate 84 is further formed so as to have between the distally directed face 86 and the top face 90 a transition face 88. In FIG. 5 the edges of faces 86, 88, and 90 are identified. Each transition face 88 is tapered in that the face 88 angles both upwardly as the face extends proximally away from the associated distally directed face 86. Each plate 84 may be formed with plural slots. A first slot, slot 92, an example first holding feature, for removably holding the bar 82 static to the saw 30, is formed in the bar so as to be forward of the proximal end of the plate 84. The plates 84 are formed so that slots 92 extend along axes that are perpendicular to the proximal-to-distal longitudinal axes through the plates. Each slot 92 is dimensioned to receive a separate one of the ribs 72 integral with the finger tips 70 and the ribs 72 are likewise dimensioned to seat in the slots 92. The second slot, i.e., a debris slot 94, formed in each plate 84 is located immediately proximal to the distal and transition faces 88 and 90, of the plates 84. Each slot 94 thus has a first section that adjacent the plate distal face that is parallel to slot 92 and a section that extends diagonally away from the first section. The second section of each slot 94 extends parallel to the transition face 88 of the plate 84 in which the slot 94 is formed.

The cartridge bar 82 also includes a spacer 98 that is sandwiched between the plates 84. Spacer 98 includes an elongated beam 102. The beam 102 has three sections, individual sections not identified with reference numbers. A first section of the beam 102 extends distally from the proximal end of the plates 92 so as to be flush with the top faces 90 of the plates. A second section of the beam 102, as it extends forward from the first section, angles downwardly so as to be flush with the transition faces 88 of the plates 84. The third section of the beam 102 extends downwardly from the second section so as to be flush with the distal faces 86 of the plates 84.

Figure 6:
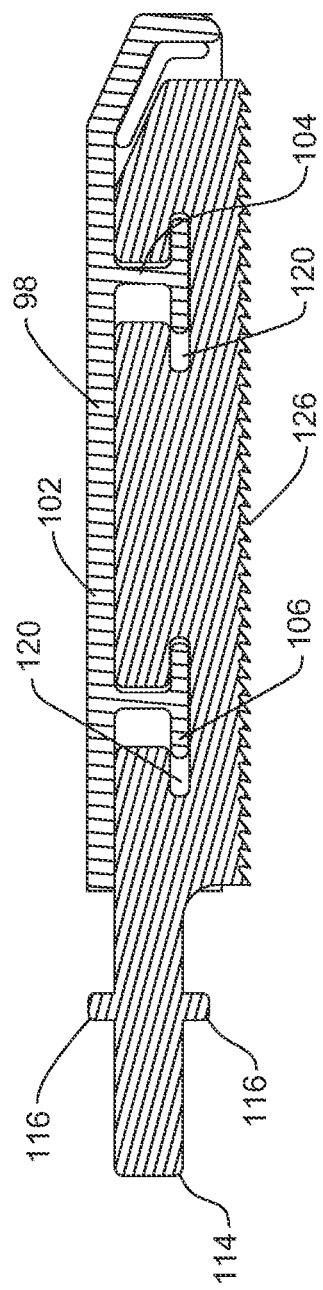
FIG. 6 is a cross sectional view of the reciprocating blade cartridge.

Spacer 98 also has two webs 104, one web being identified in FIGS. 5 and 6 with reference number 104. Webs 104 extend perpendicularly away from the first section of the beam 102. Webs 104 are parallel. The foot 106, one foot identified also part of spacer 98, is located at the end of each web 104. Feet 106 are parallel to the first section of the beam 102. Each foot 106 extends both proximally away from and distally away from the web 104 with which the foot is integral.

When the cartridge 80 is assembled, spacer 98 is welded between the plates 84. In FIG. 4 the weld lines 108 formed by the penetration welding of one plate 84 to the underlying webs 104 and feet 106 are seen.

Rack 112 includes a base 118. The base 118 is dimensioned to move in the space within the bar 82 between the plates 84 and around the web 104 and feet 106 of the spacer 98. Not identified with reference numbers are the top and distally directed surfaces of the rack base 118. Likewise not identified is the transition surface between the top and distally directed surfaces. The rack base 118 is formed with two T-shaped openings, i.e., guide slots, 120. Each opening 120 has a center section that is wider in width than the proximal to distal width across the webs 104. The end section of each opening 120 is longer in length than the length of the spacer feet 106. When the cartridge 80 is assembled, each spacer web 104 and associated foot 106 seats in one of the openings 120 in the rack base 118. Owing to the dimensioning of the components forming the cartridge, it should be understood that the rack 112 is able to move longitudinally back and forth in the bar 82.

A tail 114, also part of the rack 112, extends proximally from the base 118 so as to extend out of the bar 82. The tail has features, i.e., second holding features, that facilitate the removable coupling of the tail to the reciprocating shaft 46 internal to the saw 30. The tail may be planar in shape, and has a top to bottom height, less than the same dimension of the base. Further, the tail may be formed so that two tabs 116 extend from the opposed top and bottom sides of the tail. Tabs 116 are diametrically opposed to each other relative to the proximal to distal longitudinal axis through the tail 114.

Rack 112 also has a head 124 that extends outwardly from the base 118. The head 124 extends outwardly from the side of the base opposite the side of the base in which openings 120 are formed. The rack 112 is formed so that when the cartridge 80 is assembled, head 124 is located outside of and immediately adjacent the bottom of the bar, the portion of the rack opposite the plate top faces 90. The head 124 is formed so as to have teeth 126. The teeth 126 extend linearly, proximally to distally, along the head. The head and, more particularly the teeth have a side-to-side width that is greater than the thickness between the opposed major faces of the base of the rack 112. More specifically, the teeth have a width such that the kerf cut by the teeth can accommodate cartridge bar 82. This means that the teeth have a side to side width that is at least 0.2 mm greater than the side to side thickness across bar 82.

This saw system is prepared for use by coupling the cartridge 80 to the saw 30. An initial step of this process is the coupling of the rack tail 114 to the reciprocating shaft 46 internal to the saw 30. Tail 114 thus functions as the drive link that includes the second holding features and connects the reciprocating shaft 46 of the saw 30 to the rest of the rack 112 as may be done with the chuck 47. The clamp assembly hands 64 are secured over the cartridge so that the ribs 72 integral with the arms seat in slots 92 formed in the cartridge bar 82. This completes the removable attachment of the cartridge 80 to the saw 30. The saw 30 and cartridge 80 are ready for use.

The saw 30 and cartridge 80 are used by positioning the cartridge teeth 126 adjacent the tissue, typically bone, in which the cut is to be formed. The trigger 48 is depressed. The control module 50, in response to the detecting that depression of the trigger 18, actuates the motor 40. The actuation of the motor 40 results in the reciprocation of the reciprocating shaft 46 internal to the saw 30. The movement of the shaft 46 causes a like linear reciprocal movement of the rack 112. It should be appreciated that, as the rack 112 reciprocates, feet 106 internal to the bar 82, hold the rack 112 in the bar 82. The teeth 126 are pressed against the tissue to be cut. The reciprocation of the teeth 126 when pressed against the tissue result in the teeth forming the desired cut in the tissue.

When the saw 30 is used to cut tissue, debris formed in the cutting process enter the space between the bar plates 94. The movement of the rack 112 forces the debris out of the bar through slots 94. This prevents the debris from clogging the inside of the bar 82 to such an extent that the debris impede the reciprocation of the rack 112.

The cartridge 80 is designed so that when actuated, the only exposed portion that moves is the rack head 124. The sides of bar 82 that are pressed against tissue do not reciprocate. Since the bar 82 does not reciprocate, the possibility that the tissue could be damages such motion is eliminated.

The fact that the cartridge bar 82 does not reciprocate also means that when the distal end of the cartridge 80 is pressed against tissue, this tissue is not exposed to back and forth motion as a result of the actuation of the cartridge 80. Since this tissue is not exposed to this motion, it is not subjected to the stress of this motion that can tear or otherwise damage the tissue.

Furthermore, when the cartridge 80 is inserted in the slot of the above-discussed resection guide and actuated, the cartridge bar 82 does not reciprocate. This eliminates the wear to that otherwise occurs as a result of the metal-against-metal reciprocal movement of the whole of the blade in the resection guide. The elimination of this wear results in a like elimination of the adverse effects of this wear.

The webs 104 and feet 106 may extend through the void space in the bar 82 between the opposed inner surfaces of plates 84. Webs 104 and feet 106 thus provide the bar 82 with stiffness. The feet 106 thus perform two functions, retaining the rack 112 in the bar 82, and also providing structural strength to the bar 82.

It should likewise be understood that attachment 52 allows cartridge 80 to be used with a conventional saw 30. This means that a facility that wants to use cartridge 80 is not required to purchase a saw 30 the only purpose of which is to be used with cartridge 80.

II. Second Embodiment

Figure 7:
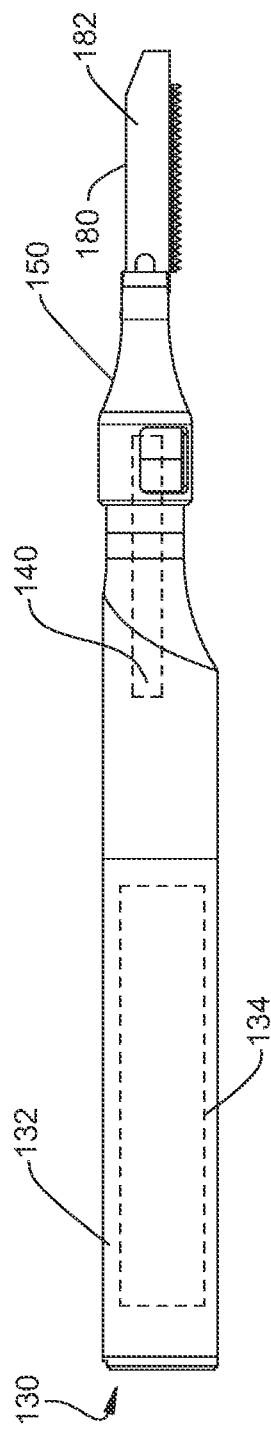
FIG. 7 is a side view of a second reciprocating saw and the complementary second reciprocating blade cartridge that is used with the saw.
Figure 8:
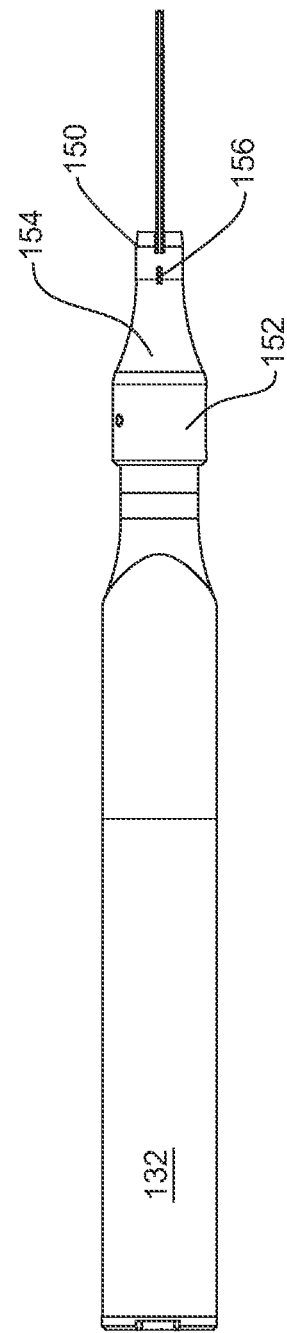
FIG. 8 is a top view of the saw and blade cartridge of FIG. 7.
Figure 9:
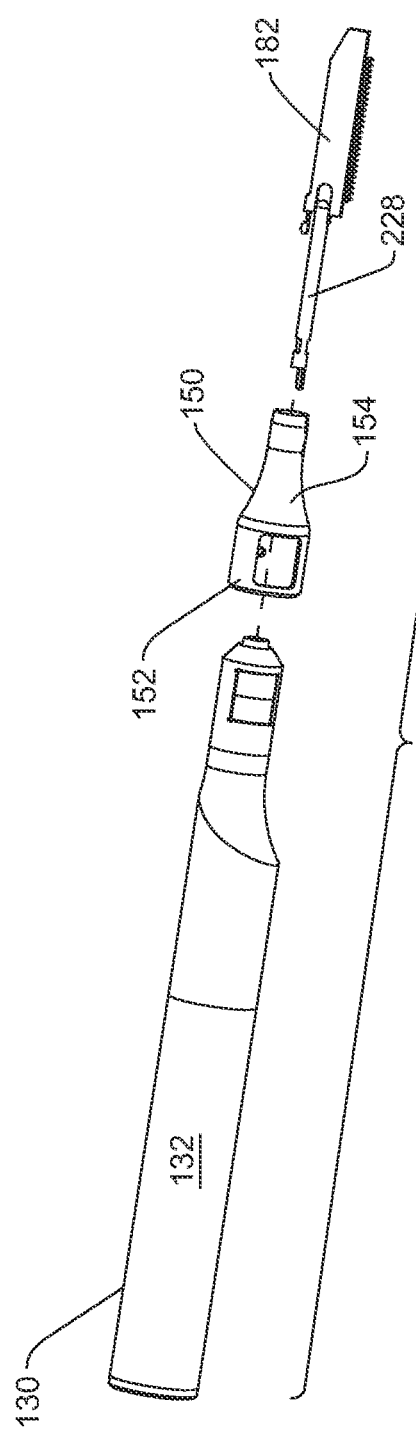
FIG. 9 is an exploded view of the saw, front end attachment and blade cartridge of FIG. 7.

FIGS. 7-9 illustrate the basic features of an alternative reciprocating saw 130 and an alternative blade cartridge 180. Saw 130 has a tubular or pencil shaped body 132. A motor, represented by a dashed rectangle 134 is disposed in the body 132. A reciprocating shaft, represented by dashed rectangle 140, extends forward of the motor. A transmission, not depicted, is located between the motor 134 and the reciprocating shaft 140. The transmission converts the rotational movement of the motor rotor into motion that reciprocates the shaft back and forth. Not shown are the components that power the motor 134. If the motor 134 is an electric motor, these components can include a control console or a battery that sources a drive current. If the motor 134 is a pneumatic motor. The drive components are the source of pressurized gas and the line over which the gas is supplied to the saw 130. If the motor 134 is a hydraulically driven motor, these components are the source of pressurized liquid and the line over which the liquid is supplied to the saw 130.

Saw 130, like saw 30, may be designed to reciprocate a conventional reciprocal saw blade.

A front end attachment 150 is removably attached to the distal end of the saw body 132. The attachment 150, together with the saw 130 and the blade cartridge 180, may collectively comprise a second example saw system. Front end attachment 150 has a base 152. Base 152 is the body of the attachment 150. Base 152 is dimensioned to seat over and be removably attached to the distal end of the saw body 132. The base 152 may be the first coupling feature by which the base is removably attached to the saw body 132. One possible coupling structure is complementary threading on the saw 130 and on the attachment base 152. An alternative coupling structure may be provided by one of the saw 130 or the attachment 150 having a snap lock that engages the other of the attachment or the saw. Still another structure for removably holding attachment 150 static to the saw body is to provide one or more compressible members that that provide a friction hold or a snap fit of the attachment 150 to the saw 130.

Forward of the base 152, the front end attachment 150 has a nose 154. The attachment 150 is formed so that as the nose 154 extends distally from the base 152, the diameter of the nose 154 decreases. The attachment 150 is generally hollow. Not identified with reference numbers are the proximal and distal openings into the nose 154. Attachment 150 is further formed so a slot 156 is formed in the nose 154. Slot 156, an example second coupling feature, is elongated in shape and has a major axis that is parallel to the longitudinal axis through the attachment 150. The attachment 150 is formed so that the distal end of the slot 156 is spaced proximally from the distal end of the nose 154. Forward of slot 156, the attachment 150 may have two diametrically opposed slots. The opposed slots extend proximally from the distal end of the attachment nose 154. One of the opposed slots is aligned with slot 156.

Figure 10:
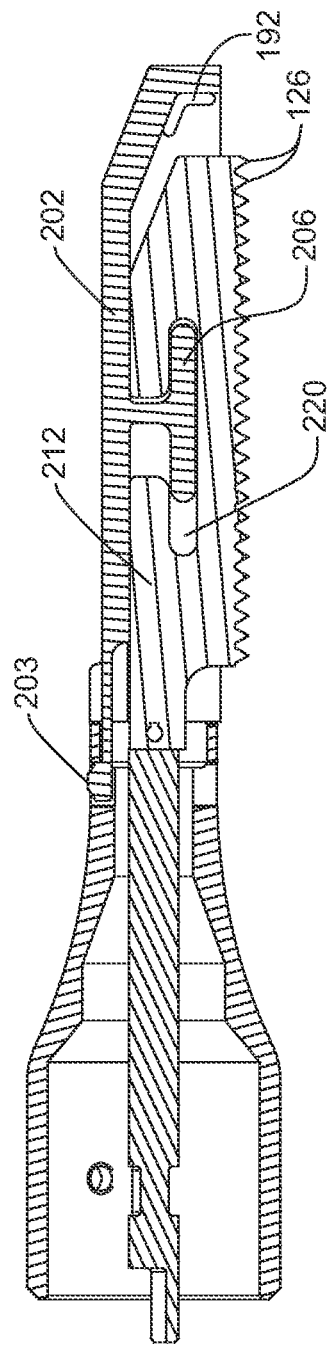
FIG. 10 is a cross sectional view of the blade cartridge of FIG. 7 coupled to the complementary front end attachment.
Figure 11:
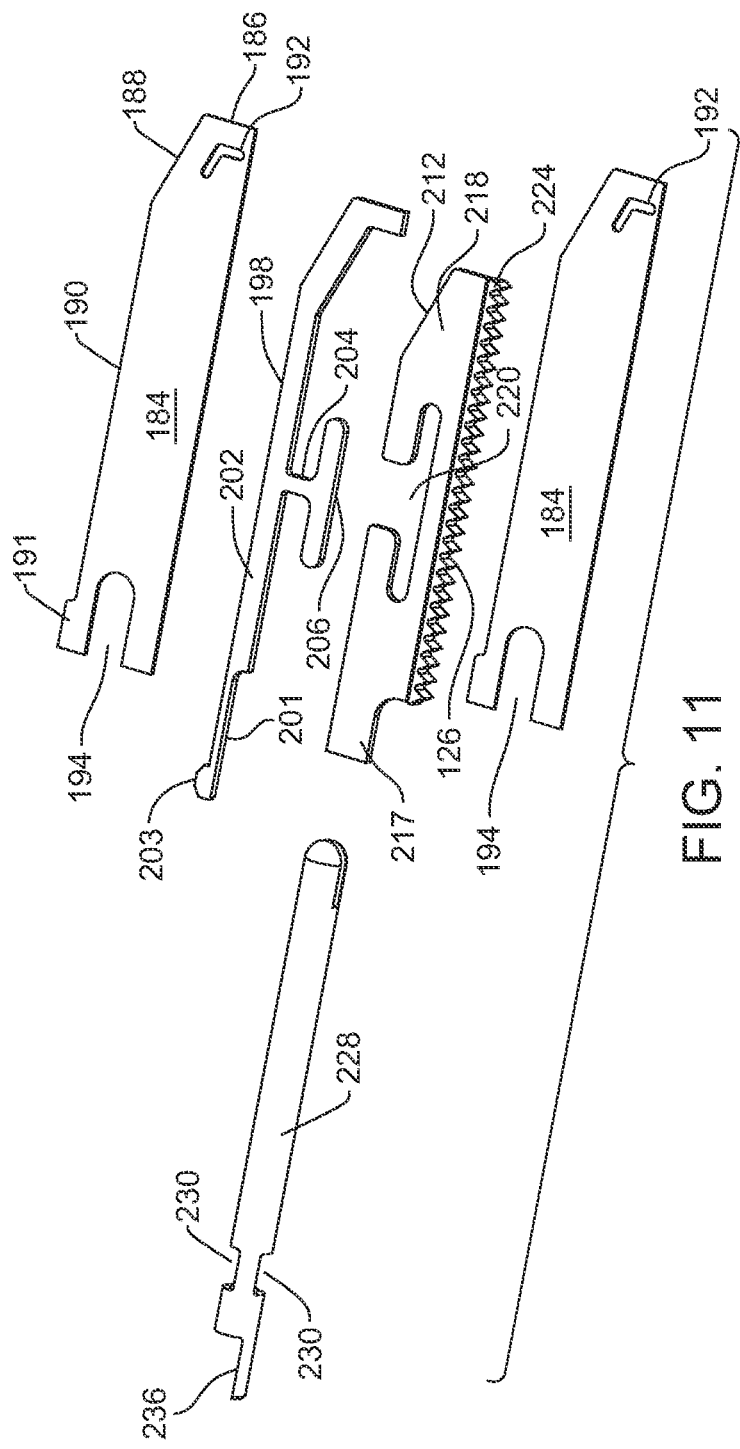
FIG. 11 is an exploded view of the reciprocating blade cartridge of FIG. 7.

Cartridge 180, as seen best in FIGS. 10 and 11 includes a static bar 182 in which a rack 212 is removably mounted. Bar 182 is formed from two plates 184. The plates 184 are generally rectangular in shape. More specifically, each plate 184 has a top face 190 the edge of one of which is identified in FIG. 11. Forward of the top face 190, each plate 184 has a distally directed face 186 the edge of one of which is identified in FIG. 11. Between the distally directed face 186 and the top face 190 there is a transition face 188, the edge of one of which is identified in FIG. 11. A plate 184 is formed so that, as the transition face 186 extends proximally from the distally directed face 186 tapers upwardly to the top face 190. The plates 184 are further formed so a rib 191 protrudes upwardly from the top faces 190. Each rib 191 extends forward a short distance, less than 1 cm, from the proximal end of the plate 184 with which the rib is integral.

Each plate 184 is formed so as to have a slot 192 that is located entirely within the plate and that is located inward of the distally directed face 190 and a short distance above the bottom face 185. Each slot 192 has an elongated section that extends parallel to the distally directed face 186 and an elongated section that extend parallel to the transition face 188. Each plate 184 also has a slot 194 that extends distally forward from proximal end of the plate. The plates are formed so the distal end perimeters of slots 194 are semi-circular in shape.

A spacer 198 is disposed between the plates 184. Spacer 198 includes a beam 202 similar to the first described beam 102. Thus beam 202 has sections that are flush with the distally directed faces 186, the transition faces 188 and the top faces 190 of the plates 184. The portion of the beam 202 that extends flush with the plate top faces 190 does not extend to the proximal end of the top faces 190. Instead, spacer 198 is further formed to have leg 201 that extends proximally between the proximal portions of the plate top faces 190. Leg 201 while integral with beam 202 has a top to bottom height less than that of beam. The spacer 198 is formed so that leg 201 extends proximally rearward beyond the plates 184. A foot 203, an example first holding feature, projects laterally upwardly from the section of the leg 201 located proximal to the plates 184.

A single web 204 extends perpendicularly from the beam 202. A foot 206 is located at the end of web 204. Web 204 and foot 206 have the same relationship to each other and beam 202 as web 104 and feet 106 due to beam 102.

When cartridge 180 is assembled, beam 202, web 204 and foot 206 are held static between the plates 184. Leg 201 and foot 203 are able to flex up and down.

Rack 212 includes a base 218. Base 218 is analogous in shape and function to base 118 of cartridge 80. Thus base 218 has a single T-shaped opening, i.e., a guide slot 220 in which the cartridge web 204 and foot 206 seat. A leg 217, also part of the rack 212, extends proximally from the base 218. Leg 217 extends into the space between the slots 194 formed in the cartridge bar 182. Rack 212 is further formed to have a head 224 from which a set of linearly aligned teeth 126 extend. Head 224 extends outwardly from the section of the base 218 adjacent the bottom faces of the bar plates 184. Again it should be understood that the head 224 and teeth 126 have a thickness greater than that of the rack leg 217 and base 218 and at least as great as the side to side thickness of the cartridge bar 182. Thus, the components of cartridge 180 are designed to that the kerf cut by the teeth is of sufficient width to accommodate the cartridge bar 182.

An arbor 228 extends proximally from the leg 217 of the rack 212. Arbor 228 is in the form of a solid cylindrical rod. Not identified with a reference number is a slot that extends proximally from the distal end of the arbor. This slot which extends across the arbor 228, is dimensioned to receive leg 217 integral with rack 212. The arbor 228 is braised or welded over the leg 217. When cartridge 180 is assembled, the distal sections of the arbor that extend outwardly of the rack 212 seat in slots 194 formed in the blade bar. The components forming the cartridge 180 are dimensioned so that the arbor 228 can reciprocate in the bar slots 194.

The proximal end of the arbor 228 is formed with retention features, i.e., example second holding features 230. The retention features are dimensioned to engage complementary retention features integral with the reciprocating shaft internal to the saw. These features when engaged, releasably hold the arbor 228 to the reciprocating shaft so the arbor reciprocates with the shaft. The retention features may include a set of notches 230 formed in the arbor.

Saw 130 and cartridge 180 are readied for use by first fitting attachment 150 over the distal end of the saw body 132. Cartridge 180 is then fitted to the saw. As part of this process, arbor 228 is coupled to the reciprocating shaft internal to the saw 130. The leg 201 integral with spacer 202 is inserted into the attachment 150 until the associated foot 203 snaps into slot 156 formed in the attachment. The seating of foot 203 in the attachment slot 156 releasably holds the cartridge bar 182 to attachment 150 and, by extension, the saw 130. As a result of the attachment of the cartridge 180 to the attachment, rib 191 and the portion of the spacer 202 sandwiched between the ribs seat in the opposed slot adjacent slot 156. The ends of plates 184 opposed to ribs 191 seat in the second slot.

The saw 130 with attached cartridge 180 is used in the same manner in which a conventional micro-style reciprocating saw is used. The actuation of the motor internal to the saw results in the back and forth movement of the reciprocating shaft. The reciprocation of the rod is, through the arbor 228 transferred to the rack 212 to cause the like movement of the rack. Owing to the dimensioning of the components, the seating of foot 206 in the rack opening 220 holds the rack for reciprocation in the cartridge bar 182. The movement of the teeth 126 saws the tissue against which the head 224 is applied.

During the cutting process, debris may enter the space between plates 184. The debris are discharged through slots 194.

III. Third Embodiment

Figure 12:
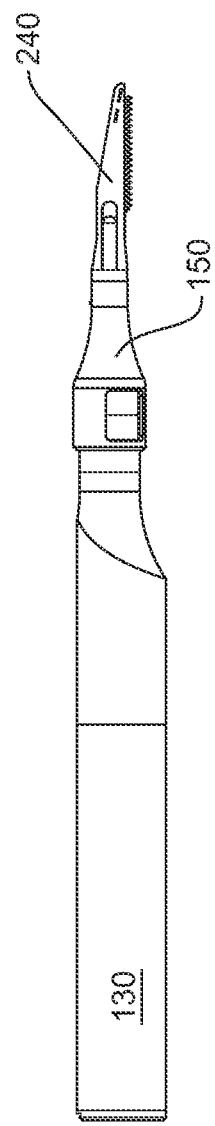
FIG. 12 is a side view of a third reciprocating blade cartridge, the cartridge being coupled to a saw.
Figure 13:
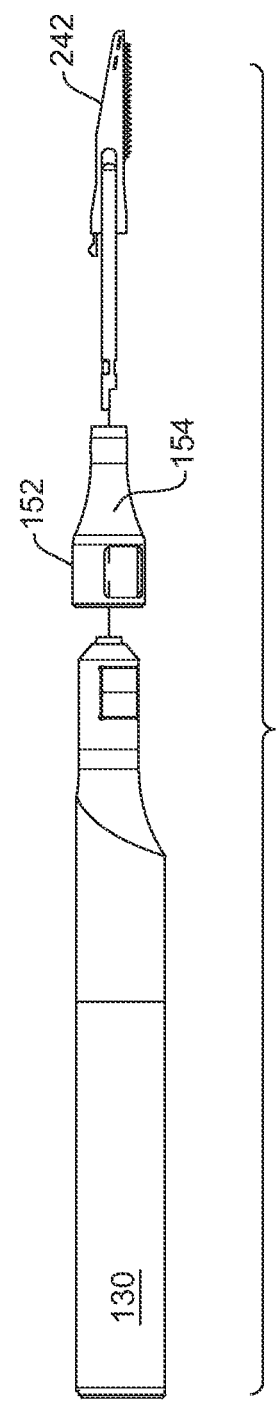
FIG. 13 is an exploded view of the basic components of the saw, front end attachment and reciprocating blade cartridge of FIG. 12.
Figure 14:
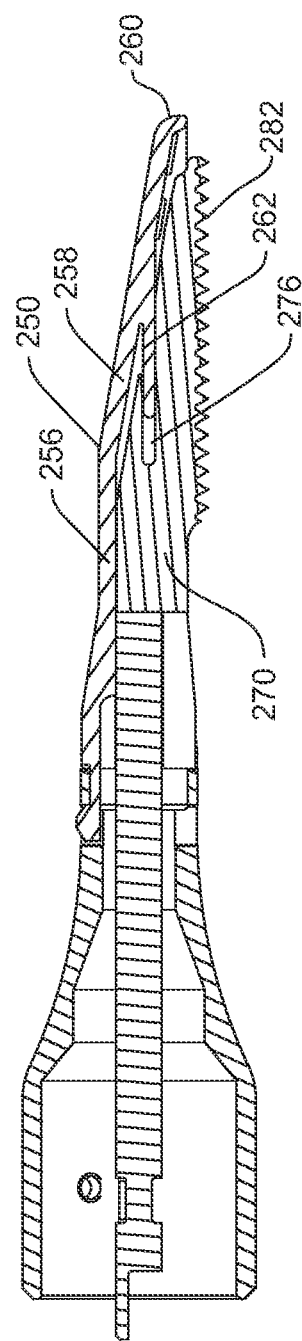
FIG. 14 is a cross sectional view of the blade cartridge of FIG. 11 coupled to the complementary saw attachment.
Figure 15:
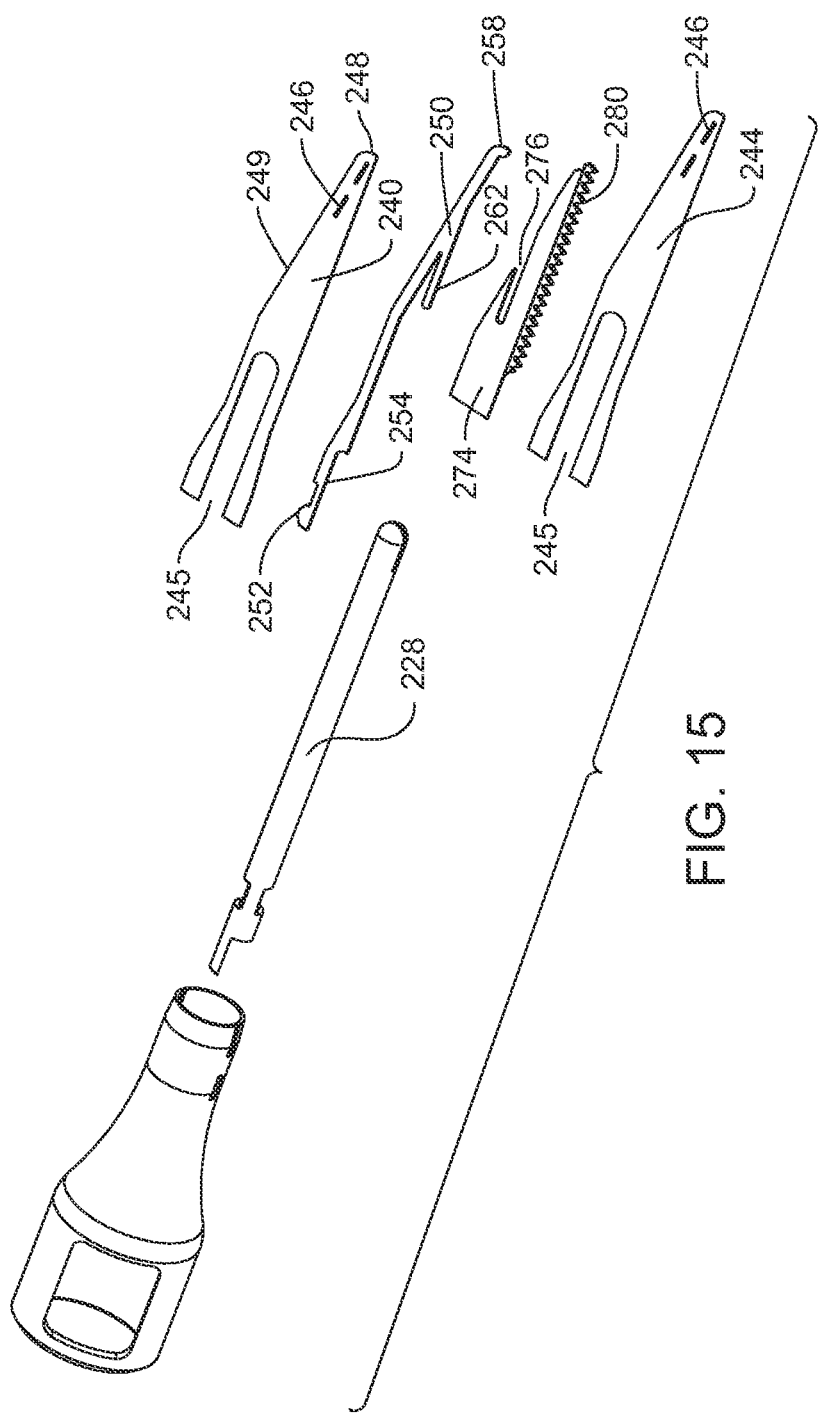
FIG. 15 is an exploded view of the reciprocating blade cartridge of FIG. 11 and the associated front end attachment.

FIGS. 12 and 13 depict a second alternative blade cartridge, cartridge 240 attached to the saw 130 and attachment 150. The attachment 150, together with the saw 130 and the blade cartridge 240, may collectively comprise a third example saw system. Cartridge 240, seen best in FIGS. 14 and 15, includes a blade bar 242. The blade bar 242 is formed from two plates 244, seen best in FIG. 15. Plates 244 have a distal end that is generally in the shape of the distal end of plates 184 of cartridge 180. Plates 244 differ from plates 184 in that plates 244 have a top face 249 that extends proximally from the front face 248, initially curves upwardly and then tapers upwardly. The tapered section of top face 249 subtends a length between 30 and 70% of the overall length of the plate 244 with which the face is integral. Plates 244 include proximally located slots 245 similar in shape and function to previously described slots 194.

Windows 246 are formed in plates 244 so as to be below and parallel to the tapered sections of plate top faces 249

A spacer 250, also part of the blade bar 242, is located between the plates 244. Spacer 250 has a foot 252 and a leg 254 similar to the foot 203 and leg 201 of cartridge 180. A beam 256 extends distally from the leg 254. Beam 256 is shaped to be flush with the top faces of the plates 244 between which the beam is disposed. Thus, the proximal section of beam 256 extends along a line that is parallel to the longitudinal axis of the cartridge. A distal section 258 of the beam 256, extending distally from the proximal section, tapers downwardly. The distal end of beam 256 is formed to define a finger 260 that is angled relative to the adjacent tapered distal section 258. Finger 260 is shaped to have an outer face, not identified, that is flush with the outer faces of the plate 244. The beam 256 is further formed to have a second finger, finger 262. Finger 262 projects proximally from the inner face of the beam section 258, the face of the beam section disposed within the plates 244. Finger 262 extends along a line that is parallel to or in registration with the longitudinal axis of the cartridge 180.

Also part of cartridge 240 is a rack 270. Rack 270 includes a base 274 dimensioned to seat in and reciprocate in the void space between the plates 244 that is proximal to spacer 250. The rack base 274 has a top edge, not identified that is tapered. The taper of the rack top edge corresponds to the taper of the beam distal section 258. Rack base 274 is formed to have an elongated slot, i.e., a guide slot 276. The slot 276 extends proximally from the tapered top edge of the rack base 274. The rack 270 is formed so that the slot 276 is positioned to and dimensioned to receive the finger 262 internal to the cartridge bar 242.

A head 280, also part of the rack 270, extends from the bottom of the rack base 274. Head 280 is the portion of the rack 270 that is located outwardly the bottom end of the blade bar 242. A section of the head 280 is located forward of the distal end of the rack base 274. The head 280 is formed to have teeth 282. The teeth are shaped to cut the tissue against which the cartridge 240 is applied. The thickness of at least the teeth is greater than the thickness across the rack base 274. More particularly, the teeth have a thickness so that the kerf cut by the teeth can accommodate the insertion of the cartridge bar into the kerf. At a minimum, the teeth 282, if not the whole of the head 280, has a thickness at least equal to the side-to-side thickness between the outer faces of plates 244.

Cartridge 240 includes the previously described arbor. Arbor 228 is welded or otherwise secured to the proximal portion of the rack base 274.

Cartridge 240 is fitted to the saw 130 using the same technique employed to fit cartridge 180 to the saw. The seating of foot 252 in the slot 156 releasably holds the cartridge to the saw 130.

Cartridge 240 is used in the manner in which cartridge 130 is employed. The seating of finger 262 in rack slot 276 holds the rack to the bar 242. Cartridge 240 has a distal section with a relative short top to bottom height. A cartridge height, from the cutting edge of the teeth 282 to the top of the blade bar of the distalmost 1 cm portion of the cartridge, may be a maximum of 1.5 cm. Such a cartridge height may facilitate the positioning of the cartridge in confined spaces such as during intra oral cutting of the mandible in orthognathic procedures or when cutting the maxilla adjacent the infraorbital nerve. Cartridge 240 is thus well suited to cut tissue in locations where it may be difficult to position a cartridge of larger bottom-to-top height.

During the cutting of tissue, the debris generated by the cutting process that enter the space between the plates 240 are discharged from the bar through windows 246.

IV. Alternative Embodiments

Alternative versions of the claimed invention may have features different from what has been described. For example, the features of the disclosed systems and components may be combined as necessary.

Likewise, the structural features may be different from what has been described. For example, the static member that extends into the slot may be a pin, inclusive of a pin-like structure. Further, such a pin or set of pins may be formed separately from the component that functions as the spacer between the bar plates. Further, the plural pins may seat in a single slot formed in the base of the rack. By extension, the slot in which this static component is disposed may be not open to the perimeter of the rack. This slot may be an elongated opening that is disposed entirely within the base of the rack.

The component or components that hold the rack to the bar may be formed integrally with one or more of the plates that form the body of the bar. Thus, as a result of a stamping or machining process, one or more of the plates is formed with a raised member. This raised member is dimensioned to seat in the complementary elongated opening in the base of the rack. The static component may be formed by the selective molding or machining of the bar of the bar or rack with which the member is integral. It should likewise be appreciated that there is no requirement this static component have any curved surfaces. Thus, this component can be rectangular or square in shape.

The slot may be a closed slot located completely in the rack.

The complementary features of the bar and rack that hold the rack to the bar while allowing the rack to move linearly may be opposite what has been disclosed above, i.e., one or more static members may extend outwardly from one or both of the opposed sides of the base of the rack. The bar may be formed with one or more elongated openings, slots, to receive the static members. Thus, when the cartridge is assembled, the rack is disposed between the plates of the bar and the static member or members integral with the rack base are disposed in the one or more slots formed in the bar. The static members and slots are formed so that the rack can move linearly in the bar. Since the static member or members are seated in the bar, the member or members hold the rack in the bar.

It should furthermore be understood that the static member, regardless of if this member is part of the bar or the rack, may be integrally formed with the component from which the member extends. The static member may be formed punching out a section of bar or rack with which the member is integral.

The rack base may subtend a surface area that is more than 50% of the surface are of the bar in which the base is seated. The rack base may alternatively subtend an area less than this percentage of the surface of the bar.

It may not be necessary to provide the bars with openings through which the debris generated in the cutting process can be discharged.

The features integral with the rack to releasably hold the rack to the reciprocating shaft employed to reciprocate the rack may be different from what has been described. Likewise, the features integral with bar that facilitates holding the bar static to the associated attachment or saw to which the cartridge is coupled may vary from what has been described.

The rack may be formed so that head and teeth project beyond the distal proximal end of the bar.

Figure 16:
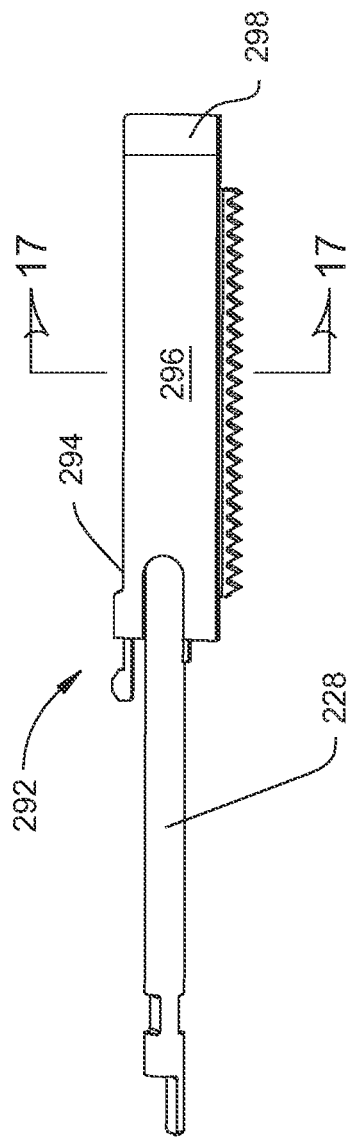
FIG. 16 is a plan view of a third reciprocating blade cartridge.
Figure 17:
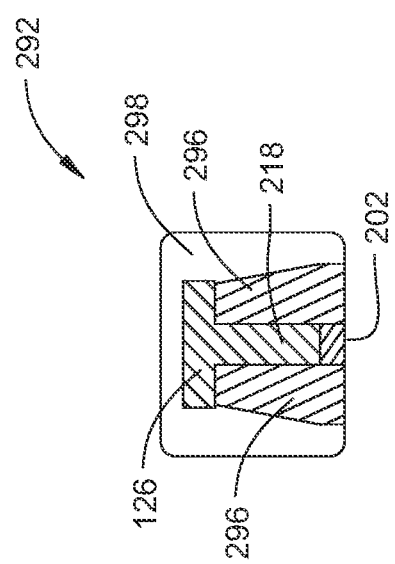
FIG. 17 is a cross sectional view taken along line 17-17 of FIG. 16 of the blade cartridge of FIG. 16.

Still another alternative blade cartridge 292 is now described with reference to FIGS. 16 and 17. Cartridge 292 includes the previously described rack 212 and arbor 228. Rack 212 is enclosed in a blade bar 294. Blade bar 294 is formed to have two opposed plates 296. Plates 296 are formed to have outer surfaces that, extending away from the side adjacent which the head 224 and teeth extend away from the bar, taper outwardly from the rack 212. Spacer 202 separates the plates 296 so as to define the void space internal to the bar 294 in which the base 218 of the rack 212 is seated. The blade bar 294 is further formed so at the distal end to have a head 298. Head 298 projects outwardly from the opposed outer surfaces of the plates 296. The blade bar 294 is further formed so that this head is located distal to the distalmost location along the bar 294 from which teeth 126 extend when rack 212 reciprocates back and forth. Cartridge 292 can be used to cut bone when it is desirable limit the depth to which the cartridge is inserted by pressing a stop against the underside of the bone being cut. One such procedure is a procedure in which it is desirable to cut across the sternum without cutting the tissue below the sternum. In this type of procedure, the protruding head 298 of the cartridge bar performs the same function as the foot of a sternum guard.

A benefit of cartridge 292, sometimes called a sternum cartridge, is that this cartridge can be fitted to a saw 30 or attachment to which any of the above disclosed cartridges 80, 180 or 240 may be is attached. This means it is possible to use a cartridge to cut through the sternum without going to the expense of providing a saw especially designed to hold a sternum guard. The tapered surfaces of the bar 294 serve to spread the sternum after the teeth 126 form the initial cut.

Another procedure in which the cartridge 292 is useful is when the cartridge 292 is used to make a cut through the skull. In this type of procedure, the stop integral with the cartridge bar is employed to ensure the cartridge is not inserted to a depth that will result in the unintended cutting of tissue below the skull.

From the above it should be understood that there is no requirement that the bar be constructed so the opposed sides are planar and parallel.

It should be appreciated that when the bar has a tapered shape the head and teeth of the rack may not have a width thereacross equal to the maximum width of the bar. Instead, the head and teeth may be formed so that the kerf cut by the rack is at a minimum of sufficient depth to receive the adjacent section of the bar from which the rack head extends. Here the adjacent section of the bar is generally understood to be the first 3 to 10 mm portion of the bar that follows the head of the rack into the bone and, typically, no more than the first 8 mm portion of the bar that follows the head of rack into the bone. The wedge forming portion or portions of the bar that follow this bottom section are understood to, after the bone is cut, further separate the cut sections of bone apart from each other.

It should further be understood that in alternative system, the saw may include features for both releasably holding the cartridge bar static to the body of the saw and releasably holding the rack to the reciprocating shaft. Thus, the features of the attachments that hold the bar static to the attachment may simply be incorporated into the saw. This saw is of use if the facility determines it is in the interest of the facility to simply have a saw available that, without an attachment, can be used to actuate the blade cartridge 80.

Accordingly, it is an object of the appended claims to cover all such variations and modifications that come within the true spirit and scope of this disclosure.

The invention claimed is:

1. A surgical saw system comprising:
   a saw including:
      a housing;
      a motor disposed within the housing; and
      a reciprocating shaft selectively reciprocated by the motor;
   a blade cartridge including:
      a bar including a first holding feature; and
      a rack, the rack moveably disposed within the bar along a proximal-to-distal longitudinal axis of the bar and is in removable engagement with the reciprocating shaft; and
   an attachment disposed between and connecting the bar of the blade cartridge to the saw housing, the attachment including:
      a coupling feature in selective releasable engagement with the first holding feature of the bar such that the coupling feature engages the first holding feature to hold the bar static when the reciprocating shaft is reciprocated by the motor to move the rack in a reciprocal motion along the proximal-to-distal longitudinal axis of the bar.

2. The saw system of claim 1, wherein the coupling feature of the attachment defines an opening dimensioned to receive the first holding feature of the bar.

3. The saw system of claim 1, wherein the coupling feature of the attachment is a finger that is dimensioned to seat in an opening defined in the bar of the blade cartridge, the opening being the first holding feature of the blade cartridge.

4. The saw system of claim 1, wherein the attachment further comprises a body including a first coupling feature in releasable engagement with a distal end of the housing to releasably hold the body of the attachment to the saw.

5. The saw system of claim 4, wherein the attachment includes two shells that form the body of the attachment, each of the shells includes a planar base and two wings that extend outwardly from opposed sides of the planar base.

6. The saw system of claim 5, wherein each of the shells is shaped so that as the wings extends away from the planar base of the shell, the wings curve away from the planar base; and wherein, when assembled, ends of the each of the wings of each of the shells face the ends of the wings of the other shell.

7. The saw system of claim 5, wherein the attachment further comprises a hand that extends distally forward from each shell, each hand includes a rectangular palm; and wherein each of the palms are dimensioned to seat over an exposed surface of the shell from which the hand extends.

8. The saw system of claim 7, wherein each of the hands comprises a finger that extends forward from each palm, each of the fingers has a main section that extends along a longitudinal axis that is parallel to a proximal-to-distal longitudinal axis through the saw.

9. The saw system of claim 8, wherein each of the fingers includes a tip that extends perpendicularly to the longitudinal axis of a main section of the finger; and a rib, that defines the coupling feature, protrudes forward from an end face of the tip of each of the fingers and the fingers are arranged so that the opposed ribs of each of the fingers face each other and engage the first holding feature of the bar to hold the bar static relative to the saw.

10. The saw system of claim 4, wherein the first coupling feature includes components attached to the body to clamp the body to the surgical saw.

11. The saw system of claim 1, wherein the rack of the blade cartridge further comprises:

a base; and a head extending from the base and located outside of a perimeter of the bar and having cutting teeth with a width defining a kerf cut by the teeth of sufficient width to accommodate the perimeter of the bar adjacent the head.

12. The saw system of claim 11, wherein:

one of the base and the bar includes an opening; and the other of the base and the bar includes a static member extending into the opening so as to retain the rack in the bar, and the opening and the static member are collectively shaped to allow the rack to engage in reciprocal movement along the proximal-to-distal longitudinal axis of the bar.

13. A surgical saw including:

a blade cartridge including:
  a bar including a first holding feature; and
  a rack, the rack moveably disposed within the bar along a proximal-to-distal longitudinal axis of the bar; and
  a drive link; and a housing;

an attachment releasably coupled to the housing for releasably holding the bar of the blade cartridge to the housing;

a motor disposed in the housing; and a reciprocating shaft connected to the motor for reciprocation by the motor;

wherein the drive link is disposed between and connecting the reciprocating shaft to the rack of the blade cartridge, the drive link arranged to impart reciprocal motion of the reciprocating shaft to the rack of the blade cartridge.

14. The surgical saw of claim 13, wherein the attachment comprises a coupling feature, the coupling feature defining an opening that is dimensioned to receive a first holding feature integral with the bar of the blade cartridge.

15. The surgical saw of claim 13, wherein the attachment comprises a coupling feature, the coupling feature including a rib extending from a finger that is dimensioned to seat in a slot defined in the bar of the blade cartridge, the slot being a first holding feature of the blade cartridge.

16. The surgical saw of claim 13, wherein the rack of the blade cartridge further comprises:

a base; and a head extending from the base and located outside of a perimeter of the bar and having cutting teeth with a width defining a kerf cut by the teeth of sufficient width to accommodate the perimeter of the bar adjacent the head.

17. The surgical saw of claim 16, wherein:

one of the base and the bar includes an opening; and the other of the base and the bar includes a static member extending into the opening so as to retain the rack in the bar, and the opening and the static member are collectively shaped to allow the rack to engage in reciprocal movement from proximal to distal to proximal along a longitudinal axis of the bar.

18. A surgical saw system including:

a blade cartridge including a bar and a rack at least partially disposed within the bar;

a saw including a reciprocating shaft, the reciprocating shaft for imparting a reciprocal motion to the rack of the blade cartridge;

an attachment connecting the blade cartridge to the saw, the attachment for releasably holding the bar of a blade cartridge static relative to the saw when the rack is reciprocated along a proximal-to-distal longitudinal axis of the bar by the saw;

a drive link disposed between and connecting the reciprocating shaft to the rack of the blade cartridge; and wherein the reciprocating shaft includes an engagement feature for releasably coupling the drive link to the reciprocating shaft, the drive link arranged to translate the reciprocal motion of the reciprocating shaft and the rack of the blade cartridge.

19. The surgical saw system of claim 18, wherein the rack of the blade cartridge further comprises:

a base; and a head extending from the base and located outside of a perimeter of the bar and having cutting teeth with a width defining a kerf cut by the teeth of sufficient width to accommodate the perimeter of the bar adjacent the head.

20. The surgical saw system of claim 19, wherein:

one of the base and the bar includes an opening; and the other of the base and the bar includes a static member extending into the opening so as to retain the rack in the bar, and the opening and the static member are collectively shaped to allow the rack to engage in reciprocal movement from proximal to distal to proximal along a longitudinal axis of the bar.

* * * * *